United States Patent [19]

Hutson, Jr. et al.

[11] 4,045,503

[45] Aug. 30, 1977

[54] ALKYL FLUORIDE STORAGE STABILIZATION AND ALKYLATION WITH STORED ALKYL FLUORIDE

[75] Inventors: Thomas Hutson, Jr.; Wayne P. Kraus, both of Bartlesville, Okla.

[73] Assignee: Phillips Petroleum Company, Bartlesville, Okla.

[21] Appl. No.: 673,324

[22] Filed: Apr. 5, 1976

[51] Int. Cl.$^2$ .................. C07C 17/42; C07C 3/54
[52] U.S. Cl. .................. 260/652.5 P; 260/683.49
[58] Field of Search .................. 260/683.49, 683.48, 260/652.5 P, 653.6, 683.51, 652.5 R

[56] References Cited

U.S. PATENT DOCUMENTS

| | | | |
|---|---|---|---|
| 2,307,799 | 1/1943 | Linn | 260/683.48 |
| 2,387,162 | 10/1945 | Matuszak | 260/683.48 |
| 2,432,030 | 12/1947 | Matuszak | 260/683.48 |
| 3,888,935 | 6/1975 | Sobel | 260/653.6 |
| 3,928,486 | 12/1975 | Sobel | 260/683.49 |

*Primary Examiner*—George Crasanakis

[57] ABSTRACT

Alkyl fluorides are stored in the presence of a paraffinic hydrocarbon diluent prior to utilization, for example, alkylation, in order to prevent degradation of the fluoride to heavy polymer oil formation.

12 Claims, No Drawings

ALKYL FLUORIDE STORAGE STABILIZATION AND ALKYLATION WITH STORED ALKYL FLUORIDE

This invention relates to improving the storage stability of alkyl fluorides. In accordance with another aspect, this invention relates to the dilution of alkyl fluorides with paraffinic hydrocarbons in an amount effective to prevent any substantial degradation of alkyl fluorides during storage and/or handling. In accordance with another aspect, this invention relates to a process of rendering alkyl fluorides storage-stable under conditions conducive to polymer formation by dilution with a paraffinic hydrocarbon in an amount sufficient to prevent loss of fluoride to heavy polymer oil formation. In accordance with a further aspect, this invention relates to a combination hydrofluorination-alkylation process comprising hydrofluorinating an olefin with HF to produce alkyl fluorides, diluting the alkyl fluorides with a paraffinic hydrocarbon prior to storage in order to prevent degradation of fluoride to heavy polymer, and subsequently subjecting the paraffin-diluted alkyl fluorides to HF alkylation to produce alkylate.

It is known in the art to hydrofluorinate olefin hydrocarbons with HF to produce alkyl fluorides and then subjecting the alkyl fluorides to alkylation with an isoparaffin in the presence of HF. As one problem encountered in the hydrofluorination of olefins to produce alkyl fluorides, it has been found that the alkyl fluorides are temperature-sensitive and have a limited storage life due to degradation of fluoride to heavy polymer. Utilization of alkyl fluorides as alkylation feed that has been exposed to conditions conducive to polymer formation produces an inferior quality alkylate. The present invention overcomes this problem by diluting alkyl fluorides with a paraffinic hydrocarbon which inhibits degradation of alkyl fluorides to heavy polymer oil formation.

Accordingly, an object of this invention is to provide a process for stabilizing alkyl fluorides.

It is another object of this invention to provide an inhibitor for stabilizing alkyl fluorides during storage.

A further object of this invention is to provide an improved combination process of hydrofluorination and alkylation to produce high quality alkylate.

Other objects, aspects, and the several advantages of the present invention will be apparent to those skilled in the art upon a study of the specification and the appended claims.

In accordance with the invention, alkyl fluorides are stabilized against degradation of fluoride to polymer by dilution with a paraffinic hydrocarbon.

In accordance with one embodiment of the invention, a process is provided for rendering alkyl fluorides storage-stable under conditions conducive to polymer formation by diluting alkyl fluorides with at least one paraffinic hydrocarbon in an amount effective to prevent any substantial degradation of alkyl fluorides during storage and/or handling and transferring from storage to a place of utilization under conditions conducive to polymer formation.

In accordance with another embodiment of the invention, high quality alkylate is produced by a combination of steps comprising hydrofluorinating an olefin-containing hydrocarbon stream with HF to produce alkyl fluorides, diluting the alkyl fluorides thus produced with at least one paraffinic hydrocarbon to render the alkyl fluorides stable against degradation to heavy polymer oil formation, and subsequently subjecting the paraffin-diluted alkyl fluorides to HF alkylation with an isoparaffin to produce said alkylate.

The conditions for carrying out the hydrofluorination and alkylation steps in the preferred embodiment of the present invention are well known in the art. The present invention is directed primarily to the dilution of alkyl fluorides with paraffinic hydrocarbons in an amount effective to prevent any substantial degradation of alkyl fluorides during storage and/or handling. The treatment or dilution of alkyl fluorides as described herein is particularly applicable in the storage and handling of alkyl fluorides produced by hydrofluorination of olefins with HF followed by HF alkylation of alkyl fluorides thus produced for the production of motor fuel alkylate.

In the first step of the present process, i.e., the hydrofluorination, a suitable olefin-containing hydrocarbon stream feed that can be employed includes generally $C_3$–$C_6$ monoolefins. The preferred olefinic reactants are those used in conventional isoparaffin-olefin alkylation processes including propylene, 1-butene, 2-butene, isobutylene, amylenes, and the like. It is presently preferred to use 1-butene for hydrofluorination and subsequently for reaction with an isoparaffin in the alkylation zone. It is also within the scope of the invention to use a mixed hydrocarbon stream comprising olefinic and isoparaffinic hydrocarbon as feed to the hydrofluorination zone. The mol ratio of isoparaffin to olefin will ordinarily range from 0.5/1 to 10/1. The hydrofluorination temperature is sufficient to hydrofluorinate the olefinic hydrocarbons present in the feed to produce alkyl fluoride and generally will be in the range of $-40°$ to $40°$ F. The pressure is ordinarily sufficient to maintain liquid phase conditions and can range from, say, about 50 to about 100 psig. The period of time for carrying out the reaction can range from 0.1 to, say, 30 minutes, or more. The volume ratio of HF to hydrocarbon can be in the range of about 0.01 to 0.5.

The alkyl fluorides produced in the first stage as described above are diluted with a suitable paraffinic hydrocarbon in an amount sufficient to prevent degradation of fluoride to heavy polymer during storage, handling, and/or transferring from storage to a place of utilization following hydrofluorination. Suitable paraffinic hydrocarbons that can be employed for dilution include those having from, say, four to about eight carbon atoms including normal butane, isobutane, pentane, isopentane, heptane, octane, and the like. The amount of paraffinic hydrocarbon added to the alkyl fluorides to render these storage-stable will vary somewhat depending upon the conditions under which the alkyl fluorides are subjecting during storage and/or handling. Generally, the amount added will be effective to prevent any substantial degradation of alkyl fluorides to polymer formation. For practical reasons, the amount of paraffin(s) hydrocarbon added will be at least 50 weight percent of the final composition and generally will be in the range of about 50 to about 95 weight percent of the final composition.

The paraffin-diluted alkyl fluorides produced as described above are passed ultimately to conventional HF alkylation wherein the alkyl fluorides are contacted with isoparaffin under conditions which produce alkylate. The conditions for carrying out the alkylation are well known, but ordinarily the temperature will be in the range of about $-40°$ to $125°$ F and sufficient pressure to maintain liquid phase conditions, for example, pressures to 50 to 200 psig. The isoparaffin to alkyl fluoride mol ratio will ordinarily range from 2/1 to 50/1 and the HF to hydrocarbon volume ratio will be in the range of about 1/1 to 20/1, and contact time of about 10 to 600 seconds.

The effluent from the alkylation can be subjected to usual phase separation to recover a hydrocarbon phase and an HF acid phase which can be recycled to the alkylation for reuse. The hydrocarbon phase can be withdrawn and passed to suitable fractionation to recover individual hydrocarbon components of the hydrocarbon phase. The paraffinic diluents contemplated herein can be readily separated from the alkylation effluent using usual fractionation or other separation techniques.

EXAMPLE

The storage stability of secondary butyl fluoride at ambient conditions was evaluated without paraffin hydrocarbon dilution and with paraffin (isobutane) hydrocarbon dilution under the same conditions.

| STORAGE DATA FOR SECONDARY BUTYL FLUORIDE | | | | |
|---|---|---|---|---|
| | (Ambient) Base Run | | Invention Run | |
| | Without Diluent | | With Diluent | |
| Days Storage (ambient) | 0 | 68 | 72 | 110 |
| Composition, Wt. %: | (Same Sample) | | (Same Sample) | |
| Ethane | — | Viscous, heavy oil. | — | — |
| Propane | 0.29 | — | 0.16 | |
| Propylene | — | Could not be analyzed. | 0.14 | — |
| Isobutane | 0.08 | — | 76.11 | 76.46 |
| Normal Butane | — | — | 2.39 | 2.94 |
| t-Butene-2 | 0.41 | — | — | — |
| cis-Butene-2 | 0.42 | — | — | — |
| Butene-1 | 4.91 | — | — | — |
| Residue ($C_6+$) | 4.41 | — | — | — |
| sec-Butyl fluoride | 89.48 | — | 21.18 | 20.44 |

Referring to the above tabulation, it can be seen that ambient storage of secondary butyl fluoride without dilution with a paraffin resulted in destruction of the fluoride either producing a viscous oil which, of course, would be unsuitable for alkylation.

When secondary butyl fluoride was stored at ambient conditions but diluted with isobutane, no loss of butyl fluoride occurred as there was no polymer formation as in the case when butyl fluoride is stored in the absence of a paraffinic diluent. The paraffin-diluted secondary butyl fluoride mixture can be charged to HF alkylation as feed.

We claim:

1. A storage-stable composition comprising an alkyl fluoride diluted with a stabilizing amount of a paraffinic hydrocarbon having from 4 to 8 carbon atoms in an amount sufficient to prevent degradation of said fluoride to polymer formation during storage and handling.

2. A composition according to claim 1 wherein the alkyl fluoride is secondary butyl fluoride and the paraffinic hydrocarbon is a $C_4$ paraffin.

3. A composition according to claim 2 wherein the paraffinic hydrocarbon is isobutane and the amount of isobutane diluent used is at least 50 weight percent of the total composition.

4. A method for rendering alkyl fluoride storage-stable under conditions conducive to polymer formation which comprises diluting said alkyl fluoride with a paraffinic hydrocarbon having from 4 to 8 carbon atoms in an amount effective to prevent any substantial degradation of alkyl fluoride during storage and handling under conditions conducive to polymer formation.

5. A composition according to claim 4 wherein the alkyl fluoride is secondary butyl fluoride and the paraffinic hydrocarbon is a $C_4$ paraffin.

6. A composition according to claim 4 wherein the paraffinic hydrocarbon is isobutane and the amount of isobutane diluent used is at least 50 weight percent of the total composition.

7. An improved process for the production of alkylate which comprises
   a. hydrofluorinating an olefin-containing hydrocarbon stream with HF under hydrofluorination conditions which produce alkyl fluorides,
   b. diluting the hydrofluorination effluent comprising alkyl fluorides with a paraffinic hydrocarbon having from 4 to 8 carbon atoms in an amount sufficient to prevent any substantial degradation of said fluoride to heavy polymer oil during storage and handling and transferring from storage to a place of utilization subsequent to hydrofluorination,
   c. storing said paraffin-diluted alkyl fluoride, and
   d. passing said paraffin-diluted alkyl fluoride obtained in step (b) after storage and handling in step (c) to alkylation and therein contacting same with an isoparaffin and HF under alkylation conditions to produce alkylate.

8. A process according to claim 7 wherein the alkyl fluoride is secondary butyl fluoride and the paraffinic hydrocarbon is a $C_4$ paraffin.

9. A process according to claim 7 wherein the paraffinic hydrocarbon is isobutane and the amount of isobutane diluent used ranges from 50 to 95 weight percent of the total composition.

10. A process according to claim 7 which comprises
    a. hydrofluorinating a monoolefin having from 3 to 6 carbon atoms under hydrofluorination conditions including a temperature ranging from $-40°$ F to $40°$ F to produce secondary alkyl fluorides,
    b. diluting the hydrofluorination effluent with a paraffinic hydrocarbon having from 4 to 8 carbon atoms in an amount of at least 50 weight percent based on the total composition, and
    c. storing the paraffin-diluted fluorides at ambient temperatures.

11. A process according to claim 10 wherein the olefin is (a) is 1-butene and the secondary alkyl fluoride is secondary butyl fluoride and further wherein said effluent is diluted with isobutane in an amount ranging from 50 to 95 weight percent of the total composition.

12. A process according to claim 10 wherein said alkylation in (b) includes a temperature in the range of $-40°$ F to $125°$ F and an isoparaffin to alkyl fluoride mole ratio ranging from 2/1 to 50/1 and an HF to hydrocarbon volume ratio in the range of about 1/1 to 20/1.

* * * * *